(12) United States Patent
Northen et al.

(10) Patent No.: US 12,172,960 B2
(45) Date of Patent: Dec. 24, 2024

(54) ORGANIC COMPOUND SALTS

(71) Applicant: GH RESEARCH IRELAND LIMITED, Dublin (IE)

(72) Inventors: Julian Northen, Sunderland (GB); Gillian Moore, Sunderland (GB); Jake Parker, Sunderland (GB)

(73) Assignee: GH RESEARCH IRELAND LIMITED, Dublin (IE)

( * ) Notice: Subject to any disclaimer, the term of this patent is extended or adjusted under 35 U.S.C. 154(b) by 0 days.

(21) Appl. No.: 18/604,747

(22) Filed: Mar. 14, 2024

(65) Prior Publication Data

US 2024/0228440 A1   Jul. 11, 2024

Related U.S. Application Data

(63) Continuation of application No. PCT/EP2023/057882, filed on Mar. 27, 2023.

(30) Foreign Application Priority Data

Mar. 27, 2022  (EP) .................................... 22000081

(51) Int. Cl.
*C07D 209/16*   (2006.01)
*A61K 31/4045*  (2006.01)

(52) U.S. Cl.
CPC ........ *C07D 209/16* (2013.01); *A61K 31/4045* (2013.01)

(58) Field of Classification Search
CPC .................................................. C07D 209/16
See application file for complete search history.

(56) References Cited

U.S. PATENT DOCUMENTS

| | | | |
|---|---|---|---|
| 11,697,638 B2 | 7/2023 | Rands et al. | |
| 11,773,063 B1 | 10/2023 | Gray et al. | |
| 2024/0101514 A1 | 3/2024 | Gray et al. | |

FOREIGN PATENT DOCUMENTS

| | | |
|---|---|---|
| WO | 2021/250434 | 12/2021 |
| WO | 2021/250435 | 12/2021 |
| WO | WO 2021/250435 A1 * | 12/2021 |

OTHER PUBLICATIONS

ACS on STN entry RN 2761182-82-3, 5-MeO-DMT HBr (entered Mar. 3, 2022).
Florence, Alastair J. "Polymorph Screening in Pharmaceutical Development." European Pharmaceutical Review, Aug. 19, 2010 (Aug. 19, 2010), XP05545733, site: www.europeanpharmaceuticalreview.com/article/3659/polymorph-screening-in-pharmaceutical-development.
Sherwood et al., "Synthesis and Characterization of 5-MeO-DMT Succinate for Clinical Use," ACS Omega, 2020, vol. 5(49): 32067-32075, doi: 10.1021/acsomega.0c05099.
Ott, Jonathan. "Pharmacotheon: Entheogenic Drugs, Their Plant Sources and History", Natural Products Co., 1996, pp. 1-639.

* cited by examiner

*Primary Examiner* — Shawquia Jackson
(74) *Attorney, Agent, or Firm* — GREENBLUM & BERNSTEIN, P.L.C.

(57) ABSTRACT

Crystalline hydrobromide salt of 5-methoxy-N,N-dimethyltryptamine (5-MeO-DMT HBr).

22 Claims, 7 Drawing Sheets

ORGANIC COMPOUND SALTS

CROSS-REFERENCE TO RELATED APPLICATIONS

This application is a continuation of PCT/EP2023/057882, filed Mar. 27, 2023, which claims the priority benefit of EP 22000081.4, filed Mar. 27, 2022. The disclosures of each of these applications is incorporated herein by reference in their entirety.

TECHNICAL FIELD

The present invention relates to 5-methoxy-N,N-dimethyltryptamine (5-MeO-DMT)hydrobromide, an acid addition salt of 5-MeO-DMT. The invention furthermore relates to the preparation and to uses of this salt, polymorphic forms, and compositions containing the salt.

BACKGROUND

5-Methoxy-N,N-dimethyltryptamine (5-MeO-DMT) has the formula shown below.

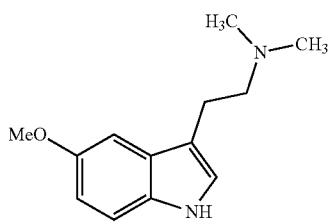 [SMILES: COc1ccc2[nH]cc(CCN(C)C)c2c1]

5-MeO-DMT is a naturally occurring serotonergic psychedelic tryptamine which acts as a 5-HT1A and 5-HT2A receptor agonist.

5-MeO-DMT was first isolated from the bark of *Dictyoloma incanescens*, but it is also contained in other plants, and it has been identified as the major active ingredient in the venom of *Incilius alvarius* (*Bufo alvarius*) toads.

Based on its physiological activities, there has recently been an interest in medical uses of 5-MeO-DMT. Such uses are disclosed in WO 2020/169850 A1 and WO 2020/169851 A1 which are directed to improved methods for the treatment of mental disorders, in particular major depressive disorder, persistent depressive disorder, anxiety disorder, posttraumatic stress disorder, body dysmorphic disorder, obsessive-compulsive disorder, eating disorder and psychoactive substance abuse, comprising administering to a patient in need thereof a therapeutically effective amount of 5-MeO-DMT.

The chemical synthesis of 5-MeO-DMT has been described in 1936 by Hoshino and Shimodaira (Bulletin of the Chemical Society of Japan, 11(3), 221-224).

Somei et al. (Chem. Pharm. Bull. 49(1) 87-96 (2001)) report syntheses of serotonin, N-methylserotonin, bufotenine, 5-methoxy-N-methyltryptamine, bufobutanoic acid, N-(indol-3-{yl)methyl-5-methoxy-N-methyltryptamine, and lespedamine. In the context of a synthesis for bufotenine, a mixture of compounds comprising 5-MeO-DMT is obtained from which the components are purified by column chromatography. 5-MeO-DMT is then recrystallised from $Et_2O$-hexane.

WO 2020/254584 A1 relates to a method of purifying 5-MeO-DMT by crystallisation and to 5-MeO-DMT in a form meeting specific purity requirements.

Certain salts of 5-MeO-DMT have also been suggested. However, the salts so far described have significant drawbacks.

Some salts show hygroscopicity or lack of stability, in particular thermal stability. Attempts to prepare salts based on dibasic acids may lead to mixed phases between mono and hemi salt versions. In WO 2020/169850 A1 and in WO 2020/169851 A1 it is contemplated that pharmaceutically acceptable salts of 5-MeO-DMT may be used. As an example for such a salt, the hydrochloride is mentioned.

WO 2021/250435 A1 describes compositions comprising a hydrochloride salt. A polymorphic form is identified which melts at about 146° C., shows an onset of thermal decomposition between 120 and 165° C. and shows significant moisture uptake above 70% RH leading to complete deliquescence at high relative humidity.

It is expected that the hygroscopic nature of the hydrochloride according to WO 2021/250435 A1 will limit its utility.

WO 2021/250435 A1 also generally refers to benzoate, fumarate, citrate, acetate, succinate, halide, fluoride, bromide, iodide, oxalate, or triflate salts, without presenting any details, such as methods of preparation or properties.

A. M. Sherwood et al. (https://dx.doi.org/10.1021/acsomega.0c05099) report on synthetical methods to obtain salts of 5-MeO-DMT and in particular describe the succinate salt (1:1).

Studies by the present inventors have, however, demonstrated that the succinate salt has a complex polymorphic landscape showing a proclivity to hydration and solvation.

Among further possible salt forming acids is fumaric acid, which is, however, suggested to be a Michael acceptor shown to form covalent products with amine-containing APIs under mild conditions. Moreover, the fumarate salt shows salt version instability due to disproportionation of the salt in various solvents.

WO 2021/250434 A1 describes a benzoate salt which can occur in various polymorphic forms.

Administration of 5-MeO-DMT and of salts thereof by various routes, among them buccal and sublingual administration, has also been suggested, in particular in WO 2020/169850 A1 and WO 2020/169851 A1.

Against this background, there is a need for further salts, and specific forms of salts, having improved properties. There is in particular a need for salts and forms of salts that are crystalline; that have favourable polymorphic properties; that have favourable flow properties; that have low hygroscopicity; that are chemically pure; that have good solubility in typical pharmaceutical vehicles, like water for injection; that show high chemical stability under conditions typically encountered during formulation and storage; and/or that show high thermal stability.

There is moreover a need for forms of 5-MeO-DMT which are especially suitable for particular routes of administration, such as buccal or sublingual administration.

SUMMARY OF THE INVENTION

The present invention relates to a crystalline hydrobromide salt of 5-methoxy-N,N-dimethyltryptamine (5-MeO-DMT HBr).

The invention provides the salt in high chemical purity, namely in a chemical purity of at least 99.5% area, preferably at least 99.8% area, in particular at least about 99.9% area, as assessed by HPLC as defined in detail herein. Preferably, the salt contains no impurity at a level of 0.1% area or higher.

The invention also provides a stable polymorphic form of the salt. This form has a melting point of 174° C. The preferred polymorphic form is characterized by an X-ray diffraction pattern comprising peaks at 14.5° 2θ±0.2° 2θ; 17.0° 2θ±0.2° 2θ; 24.2° 2θ±0.2° 2θ; measured using Cu Kα radiation. This polymorphic form can be further characterized by X-ray diffraction as set out in detail herein.

The invention also provides a salt that has favourable flow properties.

The present invention also relates to a method of preparing a crystalline hydrobromide salt, which method involves a salt forming crystallisation, in particular wherein an isopropyl alcohol/water mixture, in particular an isopropyl alcohol/water mixture having an isopropyl alcohol water ratio within the range of 80:20 to 98:2 (parts by volume), in particular of about 90:10 (parts by volume) is used as the solvent system.

The present invention furthermore provides pharmaceutical compositions comprising a salt according to the invention. The pharmaceutical composition can be in a form for administration via injection or in a form for intranasal administration.

Still further, the present invention provides pharmaceutically acceptable acid addition salts of 5-MeO-DMT in general for particular routes of administration, such as buccal or sublingual administration.

DETAILED DESCRIPTION OF THE INVENTION

Figure 1A:
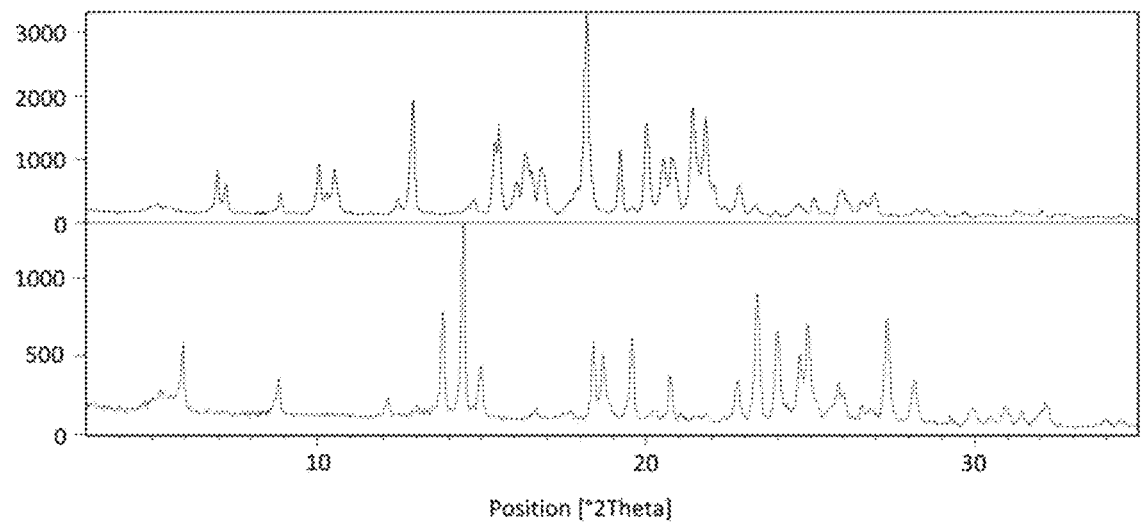
FIG. 1A shows the XRPD profile of 5-MeO DMT free base (upper diagram) and the XRPD profile of 5-MeO DMT HBr Pattern A (lower diagram)

The present invention is based on the discovery that 5-methoxy-N,N-dimethyltryptamine hydrobromide (5-MeO-DMT HBr) is an acid addition salt that has particularly advantageous properties.

In order to provide a salt suitable for pharmaceutical use, various requirements have to be observed. The salt should have positive solid-state characteristics. This includes that it should be possible to obtain the salt in crystalline form.

This form should have a high melting point and show a discrete melt endotherm. The crystalline form should not show polymorphism, or at least there should be a dominant thermodynamically stable form.

The salt should not be prone of forming solvates under preparation conditions.

The salt should have flow properties that allow easy processing.

The salt should be anhydrous and show no or only minor hygroscopicity. At the same time, it should show excellent aqueous solubility.

Still further, the salt should not only have high chemical purity but also show stability across a range of assessments both in solid form and in solution.

Relevant forms of the salt should be easy to prepare in high purity suitable for pharmaceutical use. The process should be scalable. Solvents necessary for the preparation should be nontoxic.

To address the above indicated aims, the present invention provides 5-MeO-DMT HBr.

This salt has positive solid-state characteristics. It can be obtained in a crystalline form which represents the dominant thermodynamically stable form (5-MeO-DMT HBr Pattern B). This form has a discrete melt endotherm at 174° C. and is anhydrous.

The salt has an excellent solubility in water. At the same time, it shows only minor hygroscopicity.

The salt demonstrates good stability across a range of assessments both in solid form and in solution.

In order to identify potentially useful salts, the inventors have carried out three initial salt screens using 29 acids and using isopropyl alcohol (IPA), isopropyl acetate (iPrOAc) and tetrahydrofuran:water (THF:H$_2$O) as solvent systems. A hemi salt screen with the addition of 0.5 equivalents of acid was in addition carried out.

As part of the screen, 5-MeO-DMT was charged into crystallisation tubes. Solvent was added and the resulting solutions of the API were heated to 50° C. Acids were charged in one single aliquot. The solutions were held at temperature and equilibrated for 3 hours. The solutions were then cooled to room temperature and equilibrated for 18 hours.

Where suspensions were obtained, solids were isolated by filtration and dried in vacuo at 40° C. for 18 hours.

In cases where solutions persisted, further manipulation was required to obtain an isolable solid. The following methods were used primarily to induce nucleation/crystallisation and/or obtain a solid:

Reduction of solvent volume to ~50% under a steady stream of nitrogen

Addition of anti-solvent (heptane) at both ambient and increased temperature followed by equilibration Removal of solvent by a steady stream of nitrogen Repeat scratching and trituration of resulting residue with appropriate solvent, (diethyl ether, tert-butyl methyl ether (TBME), mixture of ethanol (EtOH) and heptane) followed by equilibration of solids where a suspension was obtained Any mixtures remaining as gums were left to slowly evaporate The samples which required trituration were equilibrated for an additional 24 hours with thermal modulation to generate mobile suspensions which were then filtered.

As result of the above experiments, a crystalline hydrobromide salt of 5-methoxy-N,N-dimethyltryptamine (5-MeO-DMT) having a 1:1 stoichiometry was identified.

Accordingly, the present invention provides crystalline 5-methoxy-N,N-dimethyltryptamine (5-MeO-DMT) hydrobromide.

This salt is provided in a highly pure form, suitable for pharmaceutical use.

Purity can be analysed by reversed phase HPLC using UV detection at 220 nm.

An appropriate column is a USP 11 column (phenyl groups chemically bonded to porous silica particles, 1.5 to 10 µm in diameter), preferably a column containing particle with a size of 3.0 am and a pore size of 120 Å, wherein the phenyl groups are bonded via C4-spacers (phenylbutyl bonded phase). An appropriate column has a length of 150 mm and an inner diameter of 4.6 mm.

A commercially available column from YMC CO., LTD. (Triart Phenyl: 150×4.6 mm, 3.0 µm particle size; TPH12S03-1546PTH) can be used.

The analysis is carried out at a column temperature of 30° C.

The column is eluted at a flow rate of 1.0 ml/min using a solvent gradient based on a mobile phase A (0.05 vol. % TFA in WFI) and a mobile phase B (0.05 vol. % TFA in acetonitrile) and the solvent gradient is established by the following gradient program:

| Time (mins) | % A | % B |
| --- | --- | --- |
| 0 | 95 | 5 |
| 13 | 62 | 38 |
| 26 | 5 | 95 |
| 30.5 | 5 | 95 |
| 31 | 95 | 5 |

According to the present invention, the hydrobromide salt has a chemical purity of at least 99.5% area, preferably at least 99.8% area, in particular at least about 99.9% area, as assessed by the HPLC described above.

Further according to the invention, the salt contains no impurity at a level of 0.1% area or higher, as assessed by the HPLC method.

The hydrobromide salt of 5-MeO-DMT has been obtained in two polymorphic forms, designated herein as 5-MeO-DMT HBr Pattern A and 5-MeO-DMT HBr Pattern B. The melting behavior of both forms has been characterized.

Figure 2:
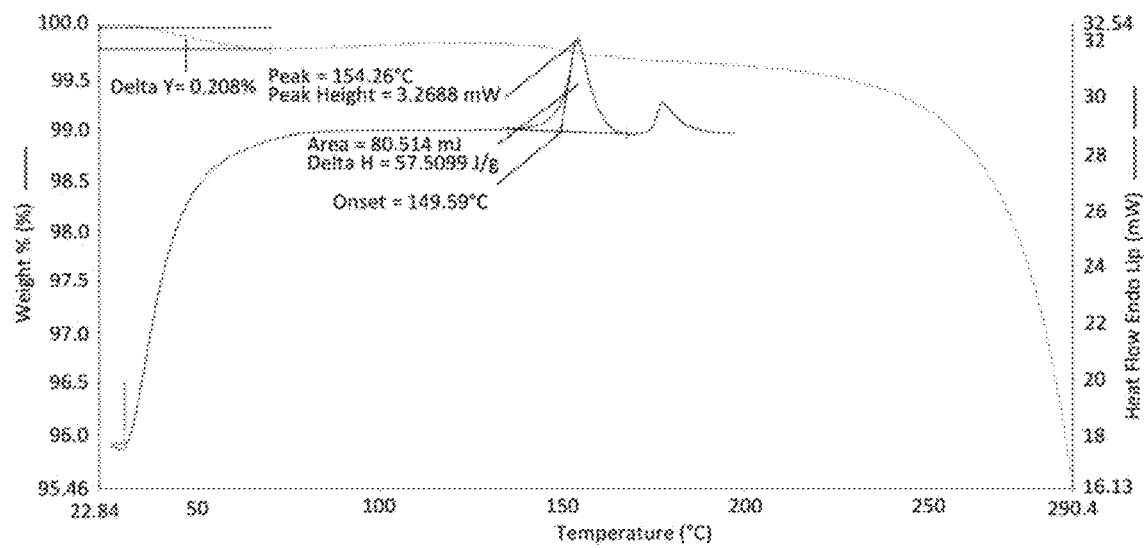
FIG. 2 shows the combined DSC/TGA thermograph of 5-MeO DMT HBr Pattern A.

The DSC thermograph of 5-MeO-DMT HBr Pattern A shows a positive thermal profile with a single endothermic event with a peak temperature of 154° C. and an onset of 150° C. (FIG. 2).

Figure 4:
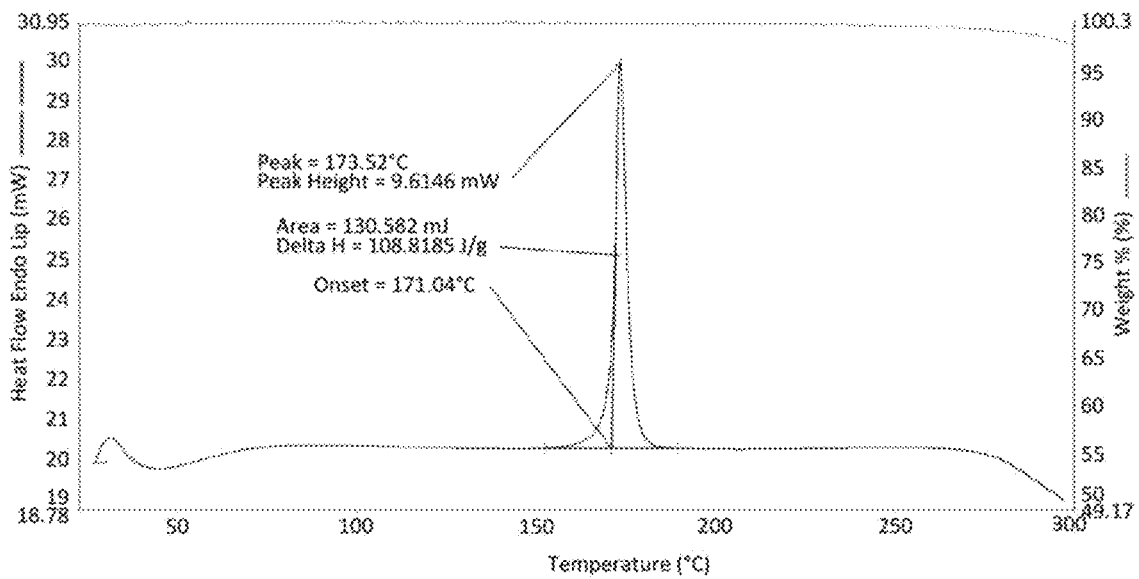
FIG. 4 shows the combined DSC/TGA thermograph of 5-MeO DMT HBr Pattern B.

The DSC thermograph of the 5-MeO-DMT HBr Pattern B shows a positive thermal profile with a single main melt endotherm with a peak temperature at 174° C. and an onset temperature of 171° (FIG. 4).

The thermal data indicate that 5-MeO-DMT HBr Pattern B represents a more stable polymorph as compared to 5-MeO-DMT HBr Pattern A. 5-MeO-DMT HBr Pattern A is metastable. According to the present invention, 5-MeO-DMT HBr Pattern B is the preferred polymorphic form of 5-MeO-DMT HBr.

Figure 3A:
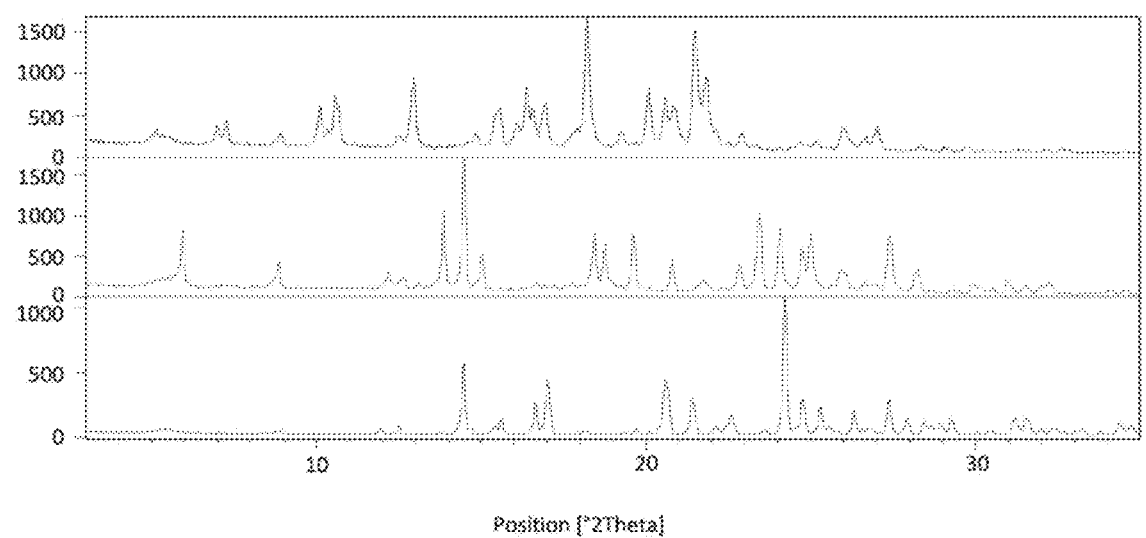
FIG. 3A shows the XRPD profile of 5-MeO DMT free base (upper diagram), the XRPD profile of 5-MeO DMT HBr Pattern A (diagram in the middle) and the XRPD profile of 5-MeO DMT HBr Pattern B (lower diagram).
Figure 3B:
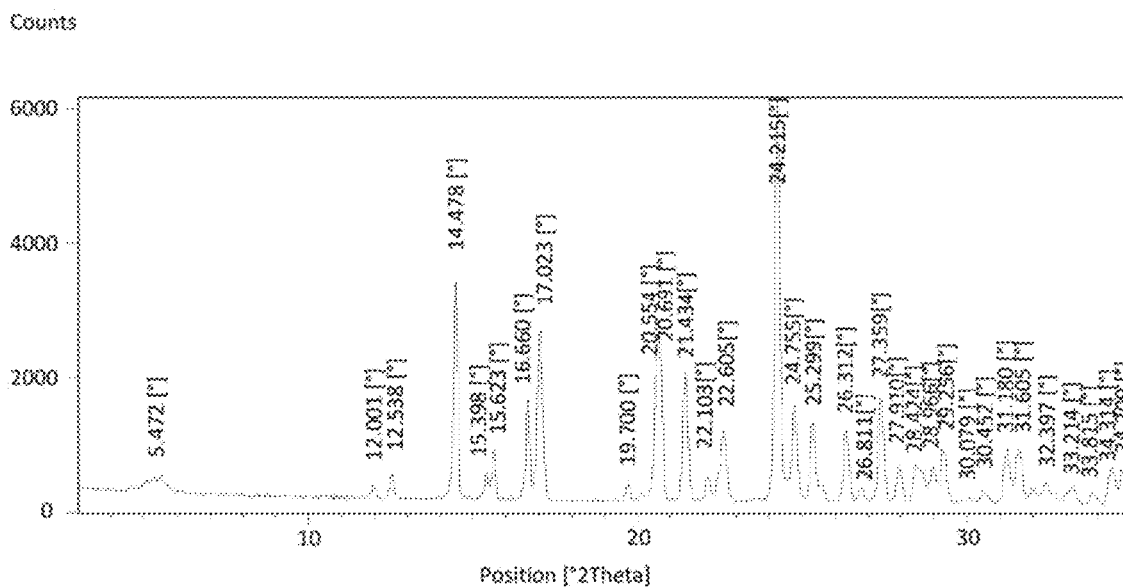
FIG. 3B shows the XRPD profile of 5-MeO DMT HBr Pattern B.

5-MeO-DMT HBr Pattern A and 5-MeO-DMT HBr Pattern B show distinctly different X-ray diffraction patterns (for a comparison, see FIG. 3A). XRPD data as measured using Cu Kα radiation are summarized in the tables below.

TABLE

Peak List 5-MeO-DMT HBr Pattern A

| Pos. [°2Th.] | Height [cts] | FWHM [°2Th.] | d-spacing [Å] | Rel. Int. [%] |
| --- | --- | --- | --- | --- |
| 5.2034 | 104.46 | 0.3070 | 16.98363 | 8.21 |
| 5.9396 | 439.05 | 0.1023 | 14.88026 | 34.51 |
| 8.8523 | 244.67 | 0.0768 | 9.98955 | 19.23 |
| 12.1675 | 116.82 | 0.1023 | 7.27424 | 9.18 |
| 13.8374 | 699.66 | 0.1023 | 6.39988 | 54.99 |
| 14.4669 | 1272.41 | 0.1279 | 6.12282 | 100.00 |
| 15.0034 | 347.50 | 0.1279 | 5.90505 | 27.31 |
| 16.6678 | 61.34 | 0.1535 | 5.31896 | 4.82 |
| 17.6493 | 51.57 | 0.3070 | 5.02530 | 4.05 |
| 18.4125 | 507.41 | 0.0768 | 4.81870 | 39.88 |
| 18.7074 | 428.81 | 0.1023 | 4.74340 | 33.70 |
| 19.5907 | 541.41 | 0.1023 | 4.53147 | 42.55 |
| 20.2668 | 67.00 | 0.1535 | 4.38179 | 5.27 |
| 20.7507 | 294.96 | 0.1279 | 4.28070 | 23.18 |
| 22.7889 | 269.39 | 0.1279 | 3.90225 | 21.17 |
| 23.3962 | 830.25 | 0.1279 | 3.80231 | 65.25 |
| 24.0107 | 574.48 | 0.1279 | 3.70638 | 45.15 |
| 24.6680 | 430.71 | 0.1023 | 3.60908 | 33.85 |
| 24.9304 | 631.71 | 0.1279 | 3.57168 | 49.65 |
| 25.8539 | 256.48 | 0.0768 | 3.44617 | 20.16 |
| 27.3385 | 673.19 | 0.1535 | 3.26230 | 52.91 |
| 28.1726 | 279.29 | 0.1535 | 3.16759 | 21.95 |
| 29.9047 | 108.27 | 0.2558 | 2.98794 | 8.51 |
| 30.9284 | 118.48 | 0.2047 | 2.89135 | 9.31 |
| 31.4301 | 83.93 | 0.1535 | 2.84633 | 6.60 |
| 32.1778 | 133.53 | 0.3070 | 2.78187 | 10.49 |
| 34.4424 | 34.57 | 0.1535 | 2.60397 | 2.72 |

The skilled person understands that, given the typical accuracy of the measurement method, when comparing XRPD data, the ° 2θ values characterizing the peak positions will be rounded to the first decimal place. Further, the skilled person understands that the rounded peak positions are associated with an error margin of ±0.2° 2θ.

5-MeO-DMT HBr Pattern A is in particular characterized by the three most intensive peaks according to the above table; the four most intensive peaks according to the above table; the five most intensive peaks according to the above table; the six most intensive peaks according to the above table; the seven most intensive peaks according to the above table; the eight most intensive peaks according to the above table; the nine most intensive peaks according to the above table.

5-MeO-DMT HBr Pattern A is in particular characterized by an X-ray diffraction pattern comprising the ten most intensive peaks from the above table, i.e., peaks at 5.9° 2θ±0.2° 2θ; 13.8° 2θ±0.2° 2θ; 14.5° 2θ±0.2° 2θ; 18.4° 2θ±0.2° 2θ; 19.6° 2θ±0.2° 2θ; 23.4° 2θ±0.2° 2θ; 24.0° 2θ±0.2° 2θ; 24.7° 2θ±0.2° 2θ; 24.9° 2θ±0.2° 2θ; 27.3° 2θ±0.2° 2θ.

TABLE

Peak List 5-MeO-DMT HBr Pattern B

| Pos. [°2Th.] | Height [cts] | FWHM [°2Th.] | d-spacing [Å] | Rel. Int. [%] |
| --- | --- | --- | --- | --- |
| 5.4720 | 212.02 | 0.6140 | 16.15078 | 3.55 |
| 12.0013 | 197.85 | 0.1023 | 7.37457 | 3.32 |
| 12.5381 | 367.20 | 0.1023 | 7.06002 | 6.16 |
| 14.4779 | 3249.59 | 0.1023 | 6.11818 | 54.48 |
| 15.3981 | 398.92 | 0.0768 | 5.75456 | 6.69 |
| 15.6229 | 738.08 | 0.1023 | 5.67227 | 12.37 |

TABLE-continued

Peak List 5-MeO-DMT HBr Pattern B

| Pos. [°2Th.] | Height [cts] | FWHM [°2Th.] | d-spacing [Å] | Rel. Int. [%] |
|---|---|---|---|---|
| 16.6598 | 1489.30 | 0.1023 | 5.32150 | 24.97 |
| 17.0228 | 2553.85 | 0.1535 | 5.20881 | 42.82 |
| 19.6998 | 274.66 | 0.1023 | 4.50663 | 4.60 |
| 20.5544 | 2121.61 | 0.1279 | 4.32113 | 35.57 |
| 20.6913 | 2227.63 | 0.1023 | 4.29286 | 37.35 |
| 21.4339 | 1859.45 | 0.1535 | 4.14578 | 31.17 |
| 22.1028 | 365.15 | 0.1279 | 4.02180 | 6.12 |
| 22.6053 | 1043.68 | 0.1535 | 3.93353 | 17.50 |
| 24.2145 | 5964.71 | 0.1791 | 3.67564 | 100.00 |
| 24.7545 | 1437.97 | 0.1535 | 3.59667 | 24.11 |
| 25.2986 | 1154.57 | 0.1535 | 3.52054 | 19.36 |
| 26.3121 | 1079.96 | 0.1535 | 3.38719 | 18.11 |
| 26.8108 | 186.67 | 0.1279 | 3.32531 | 3.13 |
| 27.3587 | 1503.07 | 0.1535 | 3.25994 | 25.20 |
| 27.9102 | 511.92 | 0.1791 | 3.19677 | 8.58 |
| 28.4235 | 513.02 | 0.1279 | 3.14019 | 8.60 |
| 28.9662 | 500.10 | 0.1535 | 3.08258 | 8.38 |
| 29.2559 | 730.94 | 0.1535 | 3.05272 | 12.25 |
| 30.0787 | 49.05 | 0.1535 | 2.97106 | 0.82 |
| 30.4516 | 133.05 | 0.2047 | 2.93552 | 2.23 |
| 31.1797 | 661.05 | 0.2047 | 2.86861 | 11.08 |
| 31.6048 | 729.23 | 0.2303 | 2.83099 | 12.23 |
| 32.3970 | 277.55 | 0.1535 | 2.76355 | 4.65 |
| 33.2137 | 215.94 | 0.1023 | 2.69744 | 3.62 |
| 33.8153 | 156.95 | 0.1791 | 2.65082 | 2.63 |
| 34.3141 | 435.92 | 0.1279 | 2.61342 | 7.31 |
| 34.7093 | 474.04 | 0.1023 | 2.58456 | 7.95 |

The skilled person understands that, given the typical accuracy of the measurement method, when comparing XRPD data, the ° 2θ values characterizing the peak positions will be rounded to the first decimal place. Further, the skilled person understands that the rounded peak positions are associated with an error margin of ±0.2° 2θ.

5-MeO-DMT HBr Pattern B is in particular characterized by the three most intensive peaks according to the above table; the four most intensive peaks according to the above table; the five most intensive peaks according to the above table; the six most intensive peaks according to the above table; the seven most intensive peaks according to the above table; the eight most intensive peaks according to the above table; the nine most intensive peaks according to the above table. In a particularly preferred embodiment, 5-MeO-DMT HBr Pattern B is characterized by an X-ray diffraction pattern comprising the ten most intensive peaks from the above table, i.e., peaks at 14.5° 2θ±0.2° 2θ; 16.7° 2θ±0.2° 2θ; 17.0° 2θ±0.2° 2θ; 20.6° 2θ±0.2° 2θ; 20.7° 2θ±0.2° 2θ; 21.4° 2θ±0.2° 2θ; 24.2° 2θ±0.2° 2θ; 24.8° 2θ±0.2° 2θ; 25.3° 2θ±0.2° 2θ; 27.4° 2θ±0.2° 2θ.

The HBr salt according to the invention, for instance, the salt as obtained by the preparation method described below, has a Carr's Index characterizing its flow properties of 25% or below, for instance, in the range of 16 to 25%, such as 20 to 25%. Additionally or alternatively, it has a Hausner Factor of 1.34 or below, for instance, in the range of 1.19 to 1.34, such as 1.26 to 1.34.

The present invention also provides methods to prepare 5-MeO-DMT HBr, in particular 5-MeO-DMT HBr Pattern B.

This salt can be prepared by salt forming crystallisation.

To this end, 5-MeO-DMT free base is dissolved in a solvent.

Suitable solvents are IPA, IPA:water, isopropyl acetate and THF:H$_2$O (97:3). A preferred solvent is IPA:water.

5-MeO-DMT free base is dissolved in the solvent at ambient temperature or with heating.

The solution of the free base is combined with HBr. HBr can be introduced in gaseous form or preferably added in the form of a solution, for instance a solution in ethanol, a solution in water or a solution on ethanol/water. Suitable solutions are, for instance, a 1M solution in ethanol or an 48 wt % solution in water.

In case of using IPA:water as a solvent system, the final IPA to water ratio in the composition is preferably within the range of 80:20 to 98:2 (parts by volume), in particular about 90:10 (parts by volume).

Combining 5-MeO-DMT free and HBr can be carried out at ambient temperature or with heating, for instance, with heating to 50° C.-70° C.

After possible removal of part of the solvent and/or cooling, a solid material will precipitate. The solid material can be isolated, for instance, by filtration, and dried. According to the invention, the solid material obtained is crystalline 5-MeO-DMT hydrobromide.

While the desired product can be obtained without using seeds, the present invention also encompasses preparation methods employing seeds, in particular seeds of 5-MeO-DMT HBr Pattern B.

According to the invention, the hydrobromide is preferably prepared from 5-MeO-DMT having a purity of at least 98% area, as determined by the HPLC method described herein.

However, salt formation can also be used for purification.

The present invention moreover relates to pharmaceutically acceptable acid addition salts of 5-MeO-DMT in general for buccal or sublingual administration.

According to the invention, a pharmaceutically acceptable acid addition salt of 5-MeO-DMT can be used as such for buccal or sublingual administration or it can be used to prepare formulations for buccal or sublingual administration.

These routes of administration involve absorption through the mucosal lining of the mouth, either sublingually (i.e., from the area beneath the tongue) or buccally (i.e., from the area between the cheek and gum). Administration via these routes can bypass the first-pass metabolism and can assure a rapid onset of action.

Formulations for buccal or sublingual administration are designed with the aim of getting dissolved or disintegrated in saliva, without the requirement of additional water.

It can therefore be advantageous to use the active ingredient in a form that has high water solubility as displayed by pharmaceutically acceptable acid addition salts of 5-MeO-DMT, in particular 5-MeO-DMT HBr.

Further, in order to avoid irritation, it is advantageous to use the active ingredient in a form that forms a solution in water having an acceptable pH value.

Suitable salts include acid addition salts, wherein the acid is selected from acetic acid, benzoic acid, citric acid, fumaric acid, hydrobromic acid, hydrochloric acid, hydrofluoric acid, hydroiodic acid, oxalic acid, succinic acid and triflic acid. A preferred example is the hydrobromide salt (5-MeO-DMT HBr).

Such acid addition salts can be prepared following procedures as illustrated on the example section for the preparation of the HBr salt.

Formulations of pharmaceutically acceptable salts of 5-MeO-DMT for buccal administration or sublingual administration include, for instance, tablets, films, sprays, and creams. Such formulations can be prepared by methods known as such.

A preferred example is a fast dissolving tablet that, when administered buccally or sublingually, disintegrates or dissolves instantaneously, releasing the drug within less than 60 seconds, such as less than 30 seconds, without the need of water.

In a further aspect, the 5-MeO-DMT HBr according to the invention can be used to prepare a pharmaceutical composition. Such a composition may comprise the salt in solid form, for instance, in the form of a dry powder, in the form of a suspension or in the form of a solution.

Pharmaceutical compositions comprising 5-MeO-DMT HBr according to the invention can be administered by various routes, for instance, via injection, via intranasal administration or via inhalation. Preferably, the compositions are administered via injection or via intranasal administration.

The following examples are intended to further illustrate the invention.

EXAMPLES

Example 1-5-MeO-DMT Used as a Starting Material

The 5-MeO-DMT was characterized to provide a set of baseline reference data for use in salt screening.

The solid was received as a beige, fine powder having a purity of 98.91% area, as determined by HPLC. The solid was shown to be crystalline by XRPD.

The DSC thermograph shows a sharp main melt endotherm with an onset temperature of 68.3° C. and a peak temperature of 70.3° C. The TGA thermograph shows the material loses no mass prior to degradation, confirming an anhydrous solid. The $^1$H NMR spectrum of the solid conforms to the molecular structure.

Example 2—Crystallization of the Hydrobromide from IPA

5-MeO-DMT (50 mg) was charged into a crystallization tube. IPA (0.5 mL, 10 vols) was added and the resulting solution of 5-MeO-DMT was heated to 50° C. HBr was charged (1M in ethanol, 1 eq) in one single aliquot. The solution was held at temperature and equilibrated for 3 hours.

The solution was then cooled to room temperature and equilibrated for 18 hours.

No precipitation was observed.

After reduction of the solvent volume to ~50% under a steady stream of nitrogen the mixture was still a solution.

Addition of anti-solvent (heptane; 10 vols.) led to a suspension. Solids were isolated by filtration and dried in vacuo at 40° C. for 18 hours.

An off-white crystalline material was obtained.

Example 3—Crystallization of the Hydrobromide from Isopropyl Acetate

5-MeO-DMT (50 mg) was charged into a crystallization tube. Isopropyl acetate (0.5 mL, 10 vols) was added and the resulting solution of 5-MeO-DMT was heated to 50° C. HBr was charged (1M in ethanol, 1 eq) in one single aliquot. The mixture was held at temperature and equilibrated for 3 hours.

After 1 hour, a suspension had formed.

The suspension was finally cooled to room temperature and equilibrated for 18 hours.

Solids were isolated by filtration and dried in vacuo at 40° C. for 18 hours.

An off-white crystalline material was obtained.

Example 4—Crystallization of the Hydrobromide from THF:H$_2$O (97:3)

5-MeO-DMT (50 mg) was charged into a crystallization tube. THF:H$_2$O (97:3) (0.5 mL, 10 vols) was added and the resulting solution of 5-MeO-DMT was heated to 50° C. HBr was charged (1M in ethanol, 1 eq) in one single aliquot. The solution was held at temperature and equilibrated for 3 hours.

The solution was then cooled to room temperature and equilibrated for 18 hours.

The salt did not readily precipitate, so additional manipulation was required.

No precipitation was observed.

After reduction of the solvent volume to ~50% under a steady stream of nitrogen and the addition of anti-solvent (heptane; 10 vols.) the formation of a gum was noted. The gum was dissipated by trituration in diethyl ether to form a suspension that was then filtered.

An off-white crystalline material was obtained.

Example 5—Characterization of the Hydrobromide (5-MeO-DMT HBr Pattern A)

Figure 1B:
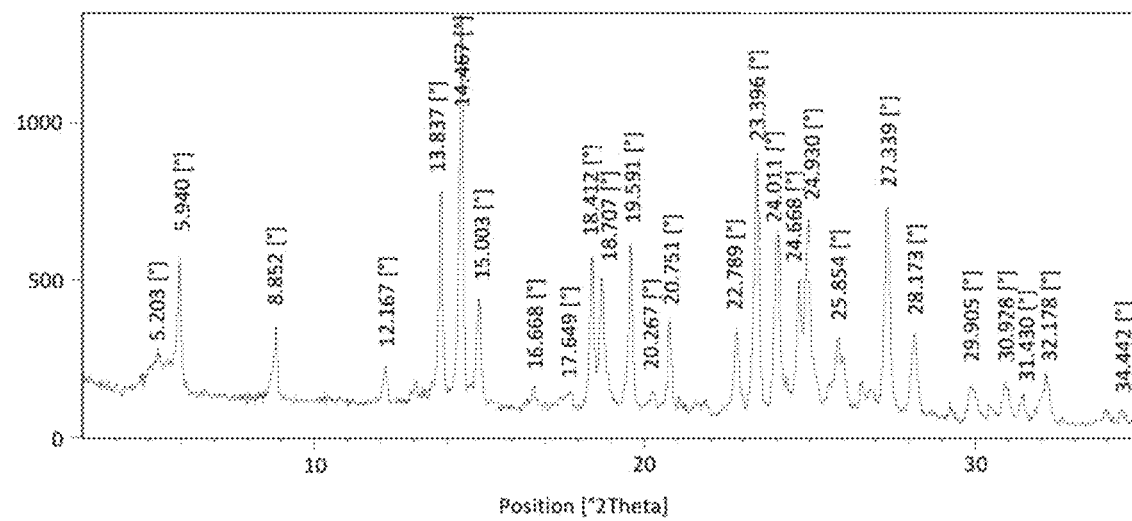
FIG. 1B shows the XRPD profile of 5-MeO DMT HBr Pattern A.

The XRPD profile of the salt as obtained in anyone of Examples 2, 3 and 4 is shown in FIG. 1A and FIG. 1B. Only one crystalline version of the HBr salt was isolated which has been designated as 5-MeO-DMT HBr Pattern A.

The X-Ray Powder Diffraction patterns were collected on a PANalytical diffractometer using Cu Kα radiation (45 kV, 40 mA), θ-θ goniometer, focusing mirror, divergence slit (½"), soller slits at both incident and divergent beam (4 mm) and a PIXcel detector. The software used for data collection was x'Pert Data Collector, version 2.2f and the data was presented using X'Pert Data Viewer, version 1.2d. XRPD patterns were acquired under ambient conditions via a transmission foil sample stage (polyimide Kapton, 12.7 μm thickness film) under ambient conditions using a PANalytical X'Pert PRO. The data collection range was 2.994-35920 with a continuous scan speed of $0.2020042s^{-1}$.

The DSC thermograph of 5-MeO-DMT HBr Pattern A was determined using a PerkinElmer Pyris 6000 DSC equipped with a 45-position sample holder. The instrument was verified for energy and temperature calibration using certified indium. A predefined amount of the sample, 0.5-3.0 mg, was placed in a pin holed aluminium pan and heated at 20° C.min$^{-1}$ from 30 to 350° C., or varied as experimentation dictated. A purge of dry nitrogen at 20 ml min$^{-1}$ was maintained over the sample. The instrument control, data acquisition and analysis were performed with Pyris Software v11.1.1 revision H. The thermograph shows a positive thermal profile with an endothermic event with a peak temperature of 154° C. and an onset of 150° C. (FIG. 2).

The corresponding TGA thermograph was determined using a PerkinElmer Pyris 1 TGA equipped with a 20-position auto-sampler. The instrument was calibrated using a certified weight and certified Alumel and Perkalloy for temperature. A predefined amount of the sample, 1-5 mg, was loaded onto a pre-tared aluminium crucible and was heated at 20° C.min$^{-1}$ from ambient temperature to 400° C. A nitrogen purge at 20 ml·min$^{-1}$ was maintained over the sample. Instrument control, data acquisition and analysis were performed with Pyris Software v11.1.1 revision H. The TGA thermograph shows a loss of 0.2% prior to the main melt endotherm indicative of minor hydration/solvation (FIG. 2).

The $^1$H NMR spectrum of 5-MeO-DMT HBr denotes a successful salt formation due to the shifts of the relevant signals; most notably the methyl groups of amine signal which has shifted from 2.2 ppm to 2.8 ppm.

Example 6—Preparation and Characterization of the Hydrobromide (5-MeO-DMT HBr Pattern B)

5-MeO-DMT HBr was scaled up to 100 mg. The methodology followed the same approach used to isolate the salts from initial screening with iPrOAc being used as the solvent.

After combining the solution of 5-MeO-DMT and the acid at 50° C., a suspension was formed. Isolation of the solids was carried out as described above.

The XRPD profile of the salt isolated following the 100 mg scale up of 5-MeO-DMT HBr is shown below. The crystallography of material differed from the freebase API as well as 5-MeO-DMT HBr Pattern A and has therefore been designated as 5-MeO-DMT HBr Pattern B (FIG. 3A, B). As no loss of water or residual solvent was indicated by TGA analysis for either anhydrous version of the HBr salts, the two different patterns of the HBr salt are a result of polymorphism.

The DSC thermograph of the 5-MeO-DMT HBr Pattern B shows a positive thermal profile with a single main melt endotherm with a peak temperature at 174° C. and an onset temperature of 171° C. (FIG. 4). The corresponding TGA thermograph shows no weight loss prior to the main melt, and represents an anhydrous version of the HBr salt (FIG. 4).

Figure 5:
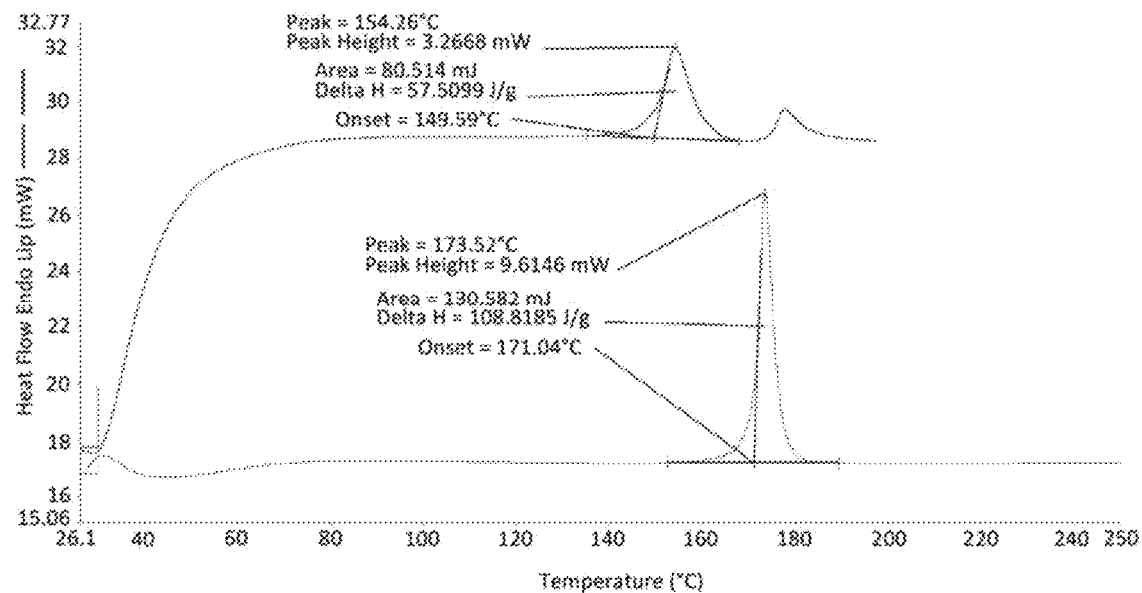
FIG. 5 shows DSC thermographs of 5-MeO DMT HBr salt versions: Pattern A (upper curve) and Pattern B (lower curve).

The comparison of the DSC thermographs of the two 5-MeO-DMT HBr salt versions shows that Pattern B has the superior thermal profile with a 20° C. higher, sharper melt, than 5-MeO-DMT HBr Pattern A (FIG. 5).

A $^1$H NMR spectrum of 5-MeO-DMT HBr Pattern B denotes a successful salt formation due to the shifts of the relevant signals; most notably the methyl groups of amine signal which have shifted from 2.2 ppm to 2.85 ppm.

Example 7—Chemical Purity

The chemical purity of the solid isolated hydrobromides was assessed by HPLC analysis. This also served the purpose to assess for any improvement as a result of salt formation.

5-MeO-DMT freebase as employed in the above salt formation experiments had a purity of 98.91% area and contains 0.20% area of an impurity having an RTT of 0.3 and 0.74% area of an impurity having an RRT of 0.96.

5-MeO-DMT HBr Pattern A as obtained in Example 2 has a purity of 99.59% area, 5-MeO-DMT HBr Pattern B (Example 6) has a purity of 99.91% area.

5-MeO DMT HPLC Method:
System: Agilent 1100/1200 series liquid chromatograph or equivalent
Column: Triart Phenyl: 150×4.6 mm, 3.0 µm particle size (Ex. YMC, Part Number: TPH12S03-1546PTH
Mobile phase A: Water: Trifluoroacetic acid (100:0.05; parts by volume)
Mobile phase B: Acetonitrile: Trifluoroacetic acid (100: 0.05; parts by volume)
Flow rate: 1.0 ml/min
Injection volume: 5 µl
Detection: 220 nm UV detection
Column temp.: 30° C.
Post run: 5 mins
Gradient:

| Time (mins) | % A | % B |
|---|---|---|
| 0 | 95 | 5 |
| 13 | 62 | 38 |
| 26 | 5 | 95 |
| 30.5 | 5 | 95 |
| 31 | 95 | 5 |

Sample preparation: 0.30 mg/ml samples prepared in acetonitrile/water (50:50)

Residual solvents are provided in the table below.

| Compound | Chemical purity by HPLC (% area) | Residual solvent by 1H NMR |
|---|---|---|
| 5-MeO DMT (Starting material) | 98.91 | 1.5% TBME |
| 5-MeO DMT HBr (Pattern A; Example 2) | 99.59 | 0.2% TBME<br>0.3% IPA |
| 5-MeO DMT HBr (Pattern B; Example 6) | 99.91 | 0.05% TBME<br>0.1% IPA |

Example 8—Solubility

5-MeO-DMT freebase and 5-MeO-DMT hydrobromide (30 mg) were weighed out into crystallisation tubes, water for injection (WFI; 150 µL, 5 vols) was charged and samples were left to equilibrate (25° C.) over 24 hours.

The free base led to a suspension. An additional 850 µl of water was added. The mixture was still a suspension. The solubility, determined following 24 hours of equilibration by an analysis of a filtrate, was 3.29 mg/ml at 25° C. The pH value of the suspension after 24 hours was 9.93, determined at 25° C.

In the case of 5-MeO-DMT HBr, a solution was obtained. The solubility determined following 24 hours of equilibration, was >200 mg/mL at 25° C. The pH value of the solution after 24 hours was 6.84, determined at 25° C.

Example 9—Stability (5-MeO-DMT HBr Pattern A)

About 10 mg of 5-MeO-DMT HBr Pattern A was weighed into a type 1 glass vial. A HDPE screw on cap was loosely fitted to the vial as to allow the ingress of moisture.

An accelerated stability study was conducted in an ICH rated 40° C./75% relative humidity stability cabinet.

Following 5 days of storage at 40° C./75% RH, the 5-MeO-DMT HBr Pattern A showed changes in the crystalline pattern by XRPD analysis. This resulting pattern has been designated as 5-MeO-DMT HBr Pattern C for descriptive purposes.

Figure 6:
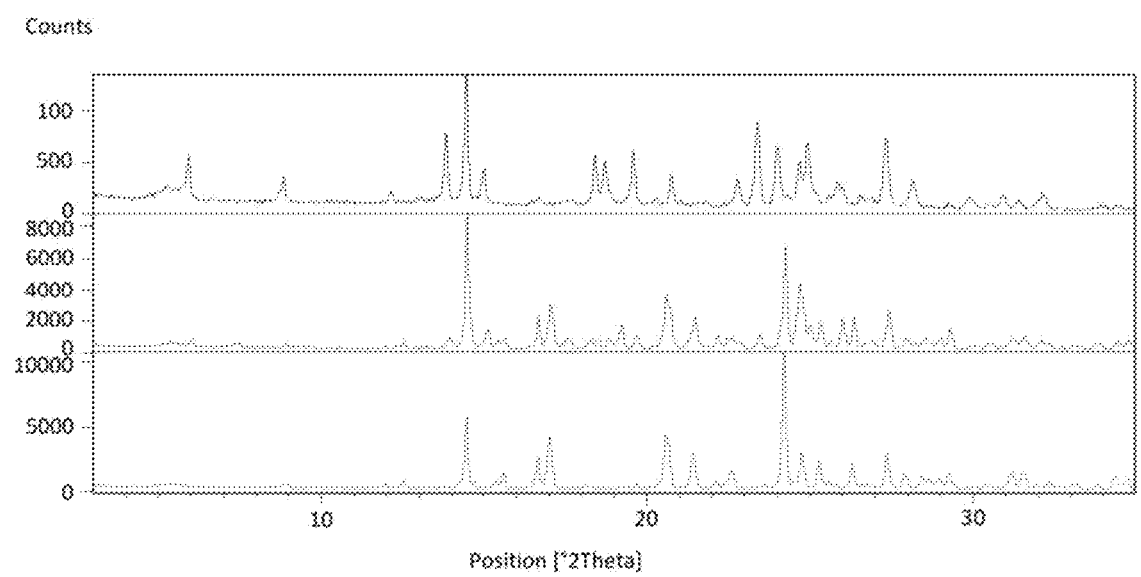
FIG. 6 shows XRPD profiles of 5-MeO DMT HBr salt versions: Pattern C (diagram in the middle) compared to Pattern A (upper diagram) and Pattern B (lower diagram).

As shown in FIG. 6, Pattern C shows similarities to Pattern B.

Figure 7:
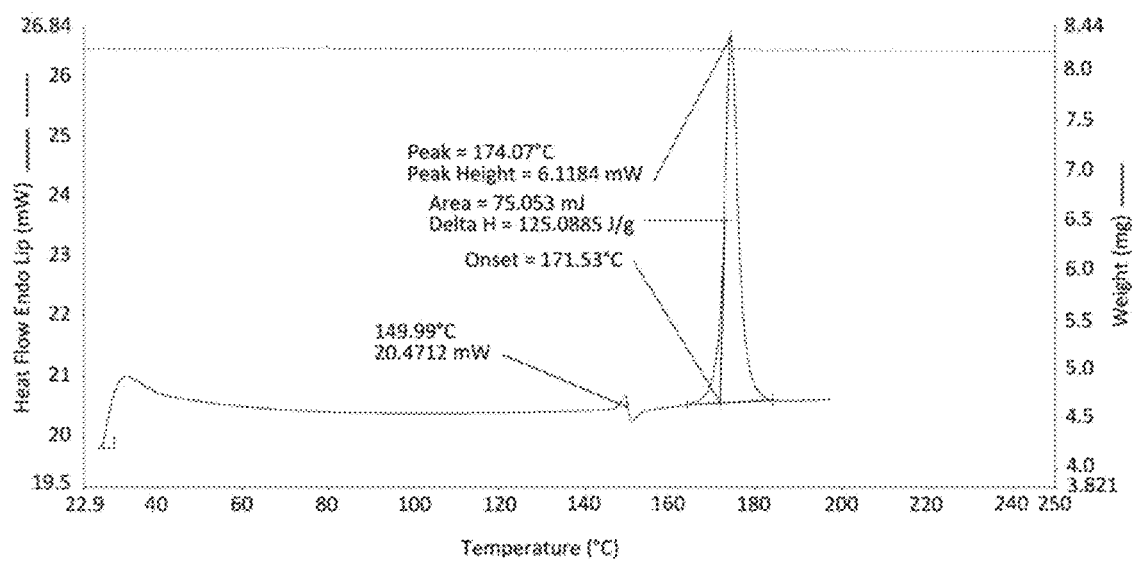
FIG. 7 shows a combined DSC/TGA thermograph of 5-MeO DMT HBr Pattern C.

The DSC thermograph of 5-MeO-DMT HBr Pattern C shows a main melt endotherm with a peak temperature of 174° C. and an onset temperature of 172° C. The small event at marked at 150° C. is postulated to be the melt of the Pattern A phase of the material followed by a recrystallisation event producing pure phase Pattern B which is known to melt at 174° C. (FIG. 7). The corresponding TGA thermograph shows no loss of mass prior to the main melt of the material indicating an anhydrous version of the HBr salt (FIG. 7).

It was concluded that Pattern C represents a mixed phase between Pattern A and Pattern B of the HBr salt.

Example 10—Stability (5-MeO-DMT HBr Pattern B)

Figure 8:
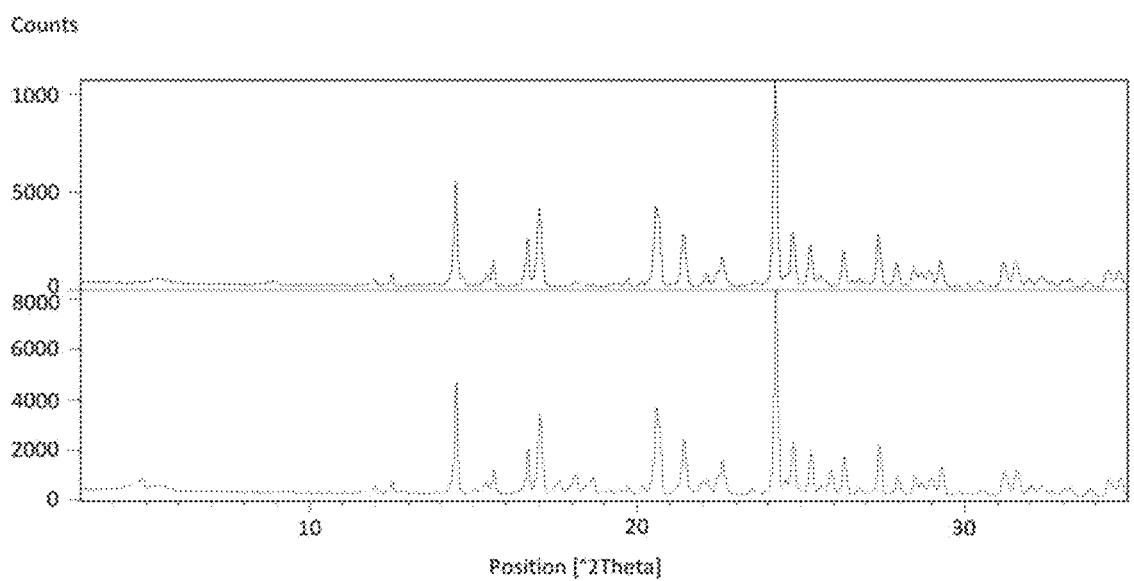
FIG. 8 shows XRPD profiles of 5-MeO DMT HBr salt version: Pattern B' (upper diagram) compared to Pattern B (lower diagram).

Following 5 days of storage at 40° C./75% RH, the 5-MeO-DMT HBr produced a crystalline pattern by XRPD analysis that was similar to the Pattern B input version. Minor differences can be seen between the two XRPD profiles including the additional peaks in the 17-19° 2θ region. This pattern has been designated as 5-MeO-DMT HBr Pattern B' for descriptive purposes (FIG. 8).

Figure 9:
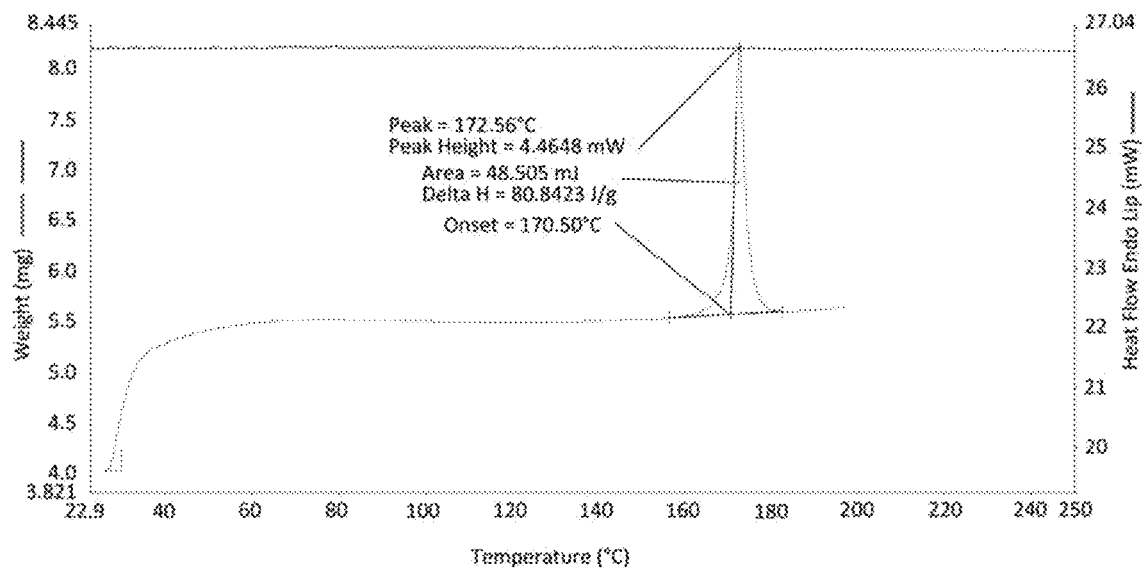
FIG. 9 shows a combined DSC/TGA thermograph of 5-MeO DMT HBr Pattern B'.

The DSC thermograph of Pattern B' 5-MeO-DMT HBr shows a positive thermal profile with a single endothermic event with a peak temperature of 173° C. (1° C. lower than 5-MeO-DMT HBr Pattern B) and an onset of 171° C. (FIG. 9). The corresponding TGA thermograph shows no loss of mass prior to the main melt endotherm representing an anhydrous version of the HBr salt (FIG. 9).

Attempts reproduce the generation of 5-MeO-DMT HBr Pattern B' were unsuccessful. 5-MeO-DMT HBr Pattern B' was also not isolated following equilibration of Pattern B at 90% relative humidity. The conclusion was therefore drawn that Pattern B' was not a true version of the HBr salt with the differences in XRPD diffractions attributed to contamination within the sample.

Example 11—Accelerated Stability Investigation of 5-MeO-DMT Salts

Following 5 days storage in an ICH rated stability cabinet at 40° C./75% RH, the chemical purity of the 5-MeO-DMT salts was assessed by HPLC.

5-MeO-DMT HBr Pattern A had an initial purity of 99.59% area. After 5 days, the purity was 99.55% area.

5-MeO-DMT HBr Pattern B had an initial purity of 99.91% area. After 5 days, the purity was 99.83% area.

The results show that the salts remained stable following 5 days storage at 40° C./75% RH with only minor decreases in chemical purity noted.

Example 12—DVS Analysis for 5-MeO-DMT HBr

Figure 10:
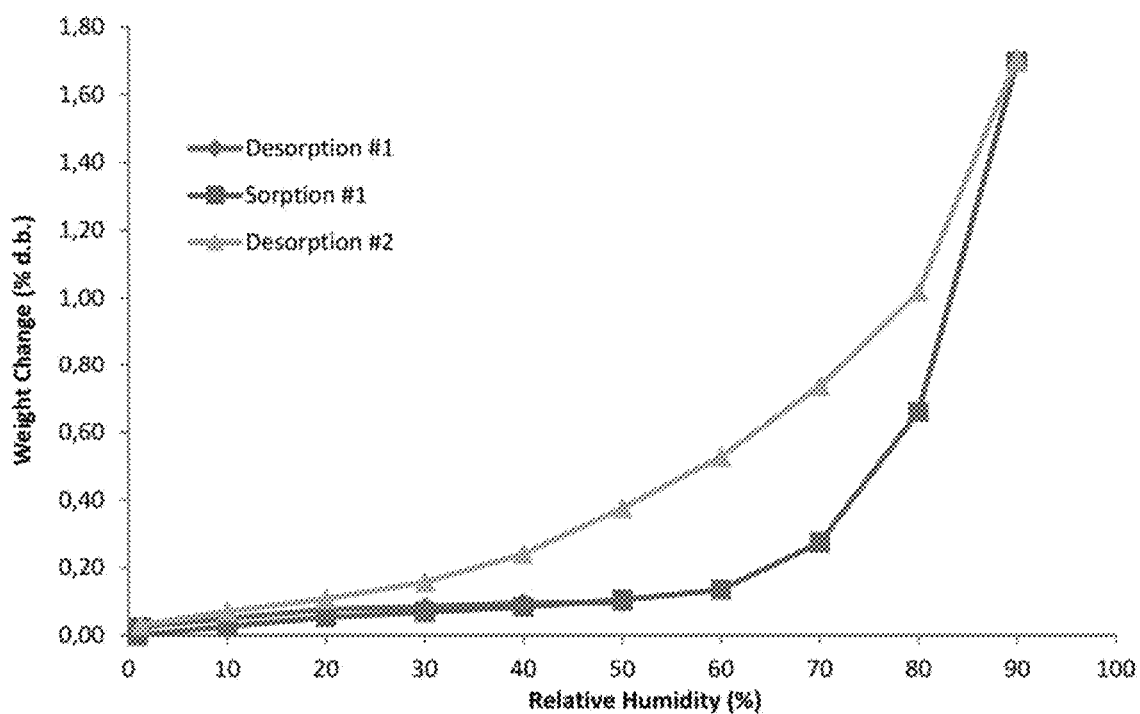
FIG. 10 shows a DVS analysis of 5-MeO DMT HBr Pattern A.
Figure 11:
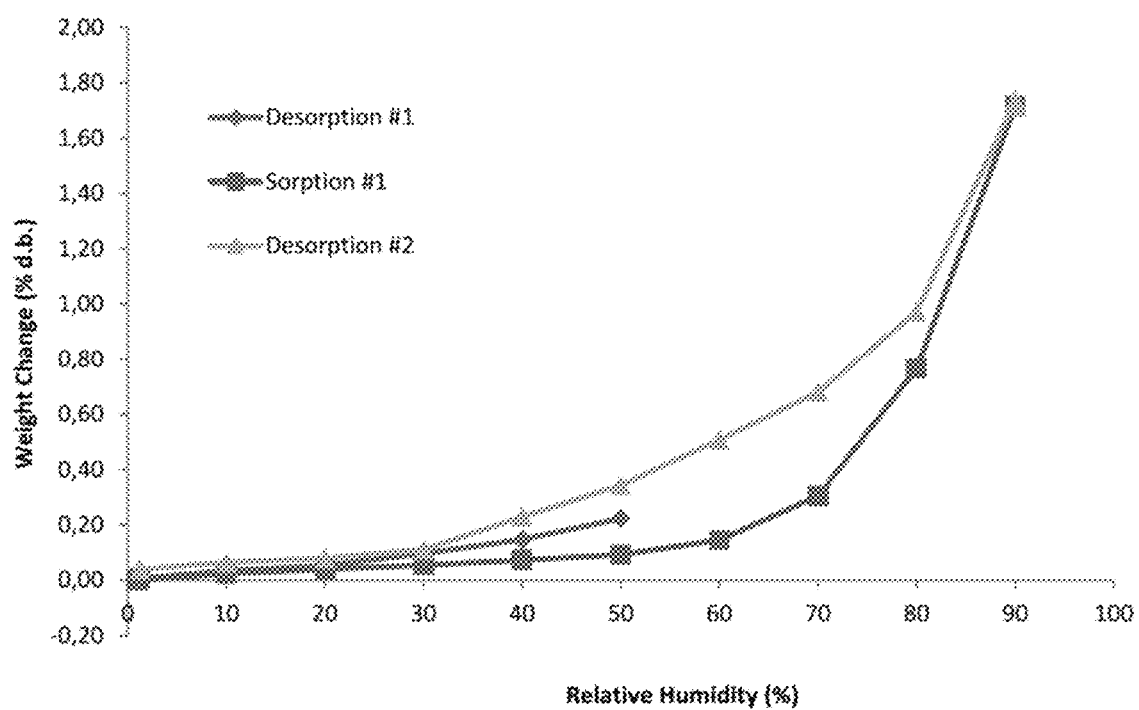
FIG. 11 shows a DVS analysis of 5-MeO DMT HBr Pattern B.

Dynamic vapor sorption (DVS) data was collected for both 5-MeO DMT HBr Pattern A and Pattern B. The DSV data are shown in FIG. 10 (Pattern A) und FIG. 11 (Pattern B). DVS profiles are almost identical. Neither form showed any modification following equilibration at extremes of relative humidity.

The DVS profile of 5-MeO DMT HBr Pattern A shows that during the first sorption cycle the solid gains 0.13% of water up to 60% RH with a further 1.56 wt % increase noted between 60% RH and 90% RH. This results in a total water absorption of 1.7 wt % over the humidity range. The water uptake is reversible as this water is lost during the subsequent desorption cycle. Hysteresis is noted with water uptake being more facile than desorption.

The DVS profile of 5-MeO DMT HBr Pattern B shows that during the first sorption cycle the solid gains 0.14% of water up to 60% RH with a further 1.57 wt % increase noted between 60% RH and 90% RH. This results in a total water absorption of 1.71 wt % over the humidity range. The water uptake is reversible as this water is lost during the subsequent desorption cycle. Hysteresis is noted with water uptake being more facile than desorption.

The DVS profiles indicate minor hygroscopicity.

Example 13—Stability in Aqueous Solution

The stability of the 5 MeO DMT HBr was evaluated in WFI for 14 days at 40° C./75% RH.

Salt was weighed into a sample vial, to which was added WFI to achieve a concentration of 100 mg/mL. The solution was then stirred at 25° C. until full dissolution was achieved. The solution was then clarified into a sample vial and was left to statically age for 14 days. The chemical purity of the solution was assessed at predetermined intervals by HPLC as described above.

| | Time (days) | | | |
|---|---|---|---|---|
| Vehicle (% Purity) | 1 | 4 | 7 | 14 |
| WFI (100 mg/mL) | 99.68 | 99.65 | 99.41 | 99.56 |

Example 14—Scale-Up of Preparation of 5-MeO DMT HBr Pattern B a) Preparation at a 5 g Scale

The formation of 5-MeO-DMT HBr Pattern B was scaled up to 5.0 g scale using previous methodology.

A stock solution of HBr acid was prepared to a 1M concentration in ethanol. 5-MeO-DMT free base (5.0 g) was weighed into a round bottom flask and dissolved in 50 mL of iPrOAc (10 vols) at 50° C. The HBr acid solution was then charged immediately at 1 equivalent. The mixture was then equilibrated at room temperature for 18 hours. The resulting suspension was isolated via vacuum filtration and dried in vacuo for 18 hours (6.28 g, 91.68% yield).

XPRD analysis of the resulting solid showed that 5-MeO-DMT HBr Pattern B was successfully prepared.

b) The Production Method/Process for Larger Scale

A salt forming crystallisation was conducted to prepare the HBr salt on a 106 g scale was conducted. 5-MeO DMT (106 g, 0.486 mol) was combined with IPA (8.9 vols, 1270 mL). The resulting solution was agitated at a rate of 275 rpm. Deionised water (90 mL) was added to the reaction vessel to deliver a slightly opaque, deep brown solution (no change from IPA alone). The solution was clarified via a 1 micron filter to a jacketed vessel without issue.

The mixture was heated to 45° C. before the dropwise addition of HBr acid (48% aq) (1.0 eq, 81 g) over 5 minutes. An additional 7 mL of water was then added to the vial containing the HBr and then added to the reaction mixture to give a final IPA to water composition of 90:10 (by volume).

The mixture was then cooled back to 43° C. and seeded with 5-MeO DMT HBr Pattern B (0.1% seed loading, 106 mg). The seed was observed to hold and crystallisation developed only marginally on holding the mixture at 43° C. for 30 minutes. The mixture was then cooled to 41° C. and agitated for an additional 1.5 hours to deliver a mild development.

The mixture was then cooled to 5° C. at 5° C./hr and equilibrated for 18 hours.

The solids were then filtered in vacuo. A facile filtration was noted via a 150 mm diameter Buchner filter/paper filter medium, deliquoring took 60 seconds for the bulk to pass through to the cake surface. A 1 volume vessel rinse was applied using 5% water/IPA, passed through the cake and a final rinse with IPA was conducted. The cake was pulled dry under air/vacuum for 20 minutes. Damp cake filter depth of 9 mm in a 150 mm diameter filter.

An off-white solid was isolated. Damp mass of 150.88 g recorded. Solids were dried at 50° C. for ca. 20 hours. 5-MeO DMT HBr was isolated as an off-white solid (78% yield).

Example 15—Further Scale-Up

To a nitrogen purged 50 L vessel was charged 5-MeO DMT (750.3 g, 3.44 mol), 2-Propanol (6160 mL) and purified water (190 mL) before stirring for 76 minutes at 15-25° C. The solution was transferred to a 10 L carboy while a particulate check was carried out before being transferred back to the 50 L vessel via 1.2 micron inline filter before the dropwise addition of polish filtered HBr acid in 2-propanol (350 mL) made using 390 ml HBr acid 48% aqueous and 3080 mL purified water over 1 hour at 15-25° C. then seeded with 5-MeO DMT HBr seed (0.8 g). The batch was stirred at 15-25° C. for 1 hour before the remaining polish filtered HBr acid in 2-propanol (3060 mL) was added dropwise over 4 hours. The batch was stirred at 15-25° C. for 1 hour then cooled to 0-10° C. at 5° C./hr and equilibrated for 24 hours. The solids were then isolated via filtration and washed with polish filtered 2-propanol (1060 mL), the solid was then dried in vacuo at 60° C.

Yield=874.3 g

Example 16—Particle Size Measurement

The particle size distribution of a sample obtained as in the above example was determined using a laser light scattering method. Results are summarized in the table below.

| Sample weight (mg) | Dv10 (μm) | Dv50 (μm) | Dv90 (μm) |
|---|---|---|---|
| 800 | 57.8 | 236 | 613 |
| 800 | 60.8 | 242 | 630 |
| 800 | 65.1 | 256 | 643 |

The HBr salt has been shown to have a $D_{50}$ of approx 240 μm with a crystal habit that is hexagonal in nature.

Example 17—Flow Properties

The bulk density and the tapped density of an HBr salt sample as obtained according to the above method was determined applying standard methods.
Bulk density: 0.19 g/cm³
Tapped density: 0.25 g/cm³
From this, the Carr's Index characterizing flow properties can be calculated (100×(Tapped density −Bulk density/ 100)). The index is 24%. The Hausner Factor (Tapped density/Bulk density) also characterizing flow properties is 1.31.
For the free base, the following values were measured:
Bulk density: 0.32 g/cm³
Tapped density: 0.54 g/cm³
Form this, a Carr's Index of 41% and a Hausner Factor of 1.68, indicating extremely poor flow properties, are obtained.

Thus, the HBr salt according to the invention has significantly improved in flow properties.

The invention claimed is:

1. A hydrobromide salt of 5-methoxy-N,N-dimethyltryptamine (5-MeO-DMT) in crystalline form, comprising peaks in an x-ray powder diffraction (XRPD) diffractogram at 2θ values of 14.5°±0.2°, 16.7°±0.2°, 20.7°±0.2°, 24.2°±0.2°, 24.8°±0.2° and 27.4°±0.2° as measured using an x-ray wavelength of 1.5406 Å.

2. A hydrobromide salt of 5-methoxy-N,N-dimethyltryptamine (5-MeO-DMT) in crystalline form, comprising peaks in an x-ray powder diffraction (XRPD) diffractogram at 2θ values of 14.5°±0.220 , 21.4°±0.2° and 24.2°±0.2° as measured using an x-ray wavelength of 1.5406 Å.

3. A hydrobromide salt of 5-methoxy-N,N-dimethyltryptamine (5-MeO-DMT) in crystalline form, comprising peaks in an x-ray powder diffraction (XRPD) diffractogram at 2θ values of 18.7°±0.2°, 19.6°±0.2° and 24.7°±0.2° as measured using an x-ray wavelength of 1.5406 Å.

4. The salt of claim 2, comprising peaks in an x-ray powder diffraction (XRPD) diffractogram at 2θ values of 14.5°±0.2°, 20.7°+0.2°, 21.4°±0.2°, 24.2°±0.2°, and 25.3°±0.2° as measured using an x-ray wavelength of 1.5406 Å.

5. A pharmaceutical composition comprising the salt of claim 1.

6. A pharmaceutical composition comprising the salt of claim 2.

7. A pharmaceutical composition comprising the salt of claim 3.

8. A pharmaceutical composition comprising the salt of claim 4.

9. A hydrobromide salt of 5-methoxy-N,N-dimethyltryptamine (5-MeO-DMT) in crystalline form, comprising peaks in an x-ray powder diffraction (XRPD) diffractogram at 2θ values of 14.5°±0.2°, 17.0°±0.2° and 24.2°±0.2° as measured using an x-ray wavelength of 1.5406 Å.

10. The salt of claim 9, comprising peaks in an x-ray powder diffraction (XRPD) diffractogram at 2θ values of 14.5°±0.2°, 16.7°+0.2°, 17.0°±0.2°, 20.7°±0.2°, 24.2°±0.2°, 24.8°±0.2°, and 27.4°±0.2° as measured using an x-ray wavelength of 1.5406 Å.

11. A hydrobromide salt of 5-methoxy-N,N-dimethyltryptamine (5-MeO-DMT) in crystalline form, comprising peaks in an x-ray powder diffraction (XRPD) diffractogram at 2θ values of 14.5°±0.2°, 17.0°±0.220 , 20.6°±0.2°, 20.7°±0.2° and 24.2°±0.2 as measured using an x-ray wavelength of 1.5406 Å.

12. The salt of claim 3, comprising peaks in an x-ray powder diffraction (XRPD) diffractogram at 2θ values of 13.8°±0.2°, 14.5°±0.2°, and 23.4°±0.2° as measured using an x-ray wavelength of 1.5406 Å.

13. The salt of claim 3, comprising peaks in an x-ray powder diffraction (XRPD) diffractogram at 2θ values of 13.8°±0.2°, 14.5°±0.2°, 23.4°±0.2°, 27.3°±0.2°, and 24.9°±0.2° as measured using an x-ray wavelength of 1.5406 Å.

14. A pharmaceutical composition comprising the salt of claim 9.

15. A pharmaceutical composition comprising the salt of claim 10.

16. A pharmaceutical composition comprising the salt of claim 11.

17. A pharmaceutical composition comprising the salt of claim 12.

18. A pharmaceutical composition comprising the salt of claim 13.

19. A hydrobromide salt of 5-methoxy-N,N-dimethyl-tryptamine (5-MeO-DMT) in crystalline form, comprising peaks in an x-ray powder diffraction (XRPD) diffractogram at 2θ values of 14.5°, 16.7°, 20.7°, 24.2°, 24.8° and 27.4° as measured using an x-ray wavelength of 1.5406 Å.

20. A hydrobromide salt of 5-methoxy-N,N-dimethyl-tryptamine (5-MeO-DMT) in crystalline form, comprising peaks in an x-ray powder diffraction (XRPD) diffractogram at 2θ values of 14.5°, 21.6° and 24.2° as measured using an x-ray wavelength of 1.5406 Å.

21. A hydrobromide salt of 5-methoxy-N,N-dimethyl-tryptamine (5-MeO-DMT) in crystalline form, comprising peaks in an x-ray powder diffraction (XRPD) diffractogram at 2θ values of 18.7°, 19.6° and 24.7° as measured using an x-ray wavelength of 1.5406 Å.

22. The salt of claim 20, comprising peaks in an x-ray powder diffraction (XRPD) diffractogram at 2θ values of 14.5°, 20.7°, 21.6°, 24.2° and 25.3° as measured using an x-ray wavelength of 1.5406 Å.

* * * * *

UNITED STATES PATENT AND TRADEMARK OFFICE
CERTIFICATE OF CORRECTION

PATENT NO. : 12,172,960 B2
APPLICATION NO. : 18/604747
DATED : December 24, 2024
INVENTOR(S) : J. Northen et al.

Page 1 of 1

It is certified that error appears in the above-identified patent and that said Letters Patent is hereby corrected as shown below:

In the Claims

Column 16, Line 13 (Claim 2), please change "0.220 ," to --0.2°,--.
Column 16, Line 46 (Claim 11), please change "0.220 ," to --0.2°,--.

Signed and Sealed this
Twentieth Day of May, 2025

Coke Morgan Stewart
*Acting Director of the United States Patent and Trademark Office*